United States Patent [19]
Sakurai et al.

[11] Patent Number: 5,211,625
[45] Date of Patent: May 18, 1993

[54] ULTRASONIC TREATMENT APPARATUS

[75] Inventors: Tomohisa Sakurai; Tetsumaru Kubota, both of Hachioji; Tatsuya Kubota, Sagamihara; Hiroaki Kagawa, Hachioji; Yuichi Ikeda, Hachioji; Mitsumasa Okada, Hachioji; Hitoshi Karasawa, Hachioji; Hideo Nagazumi, Hachioji; Kazuya Hijii, Hachioji; Toshihiko Suzuta, Hachioji; Masahiro Kudo, Hachioji; Kenji Yoshino, Tama; Tadao Hagino, Yokohama, all of Japan

[73] Assignee: Olympus Optical Co., Ltd., Tokyo, Japan

[21] Appl. No.: 670,535

[22] Filed: Mar. 15, 1991

[30] Foreign Application Priority Data

Mar. 20, 1990 [JP] Japan ............................ 2-71023
Jul. 31, 1990 [JP] Japan ............................ 2-203573

[51] Int. Cl.5 ............................................. A61B 17/20
[52] U.S. Cl. ...................................... 604/22; 128/24 AA; 606/169; 606/39
[58] Field of Search ............ 604/22; 128/24 AA, 159; 606/169–171, 39, 32

[56] References Cited

U.S. PATENT DOCUMENTS

| | | | |
|---|---|---|---|
| 3,945,375 | 3/1976 | Banko | 604/22 |
| 4,223,676 | 9/1980 | Wuchinich et al. | 604/22 |
| 4,750,488 | 6/1988 | Wuchinich et al. | 604/22 |
| 4,804,364 | 2/1989 | Dieras et al. | 604/22 |
| 4,867,141 | 9/1989 | Nakada et al. | 604/22 |
| 4,931,047 | 6/1990 | Broadwin et al. | 604/22 |
| 4,989,588 | 2/1991 | Kubota et al. | 604/22 |
| 5,011,471 | 4/1991 | Miyazaki et al. | 606/127 |
| 5,015,227 | 5/1991 | Broadwin et al. | 604/22 |
| 5,038,756 | 8/1991 | Kepley | 128/24 AA |

FOREIGN PATENT DOCUMENTS 0282684 9/1988 European Pat. Off. .
WO89/02725 4/1989 PCT Int'l Appl. .

Primary Examiner—Stephen C. Pellegrino
Assistant Examiner—Michael Rafa
Attorney, Agent, or Firm—Frishauf, Holtz, Goodman & Woodward

[57] ABSTRACT

An ultrasonic treatment apparatus comprises a hand piece, and an RF power supply unit. The hand piece includes vibrator cover, a sheath connected thereto, a hollow cylindrical member, an ultrasonic vibrator in the cover for generating ultrasonic vibrations, a probe arranged in the sheath, for externally transmitting ultrasonic vibrations generated by the vibrator, and a cord for transmitting a high-frequency current from the RF power supply unit to the probe. The cover and sheath are composed of an insulating member, for preventing the high-frequency current transmitted by the probe from being externally leaked.

8 Claims, 14 Drawing Sheets

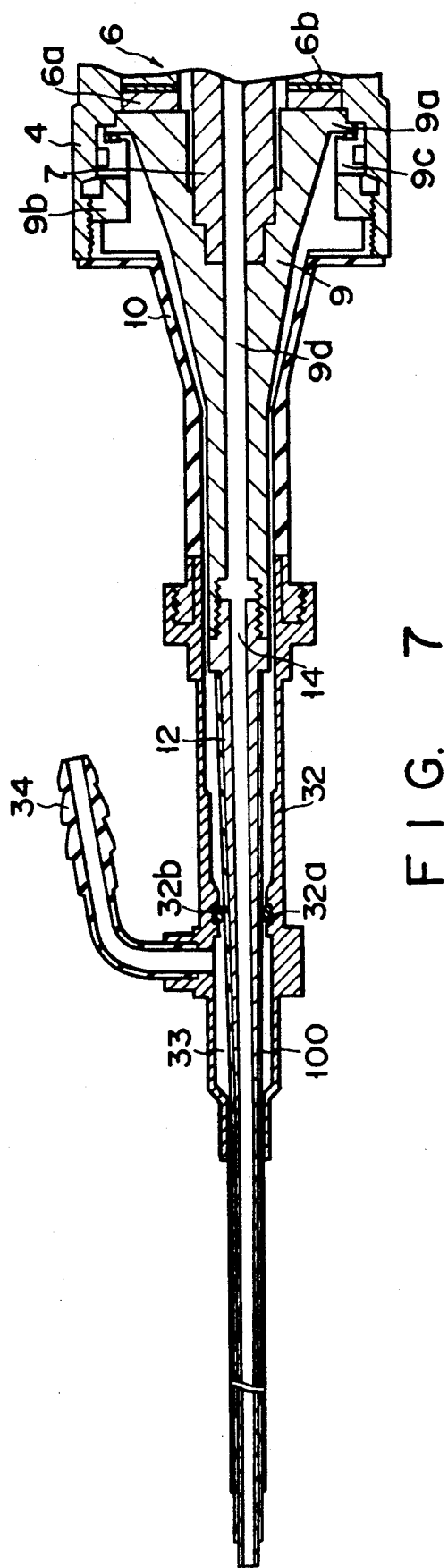
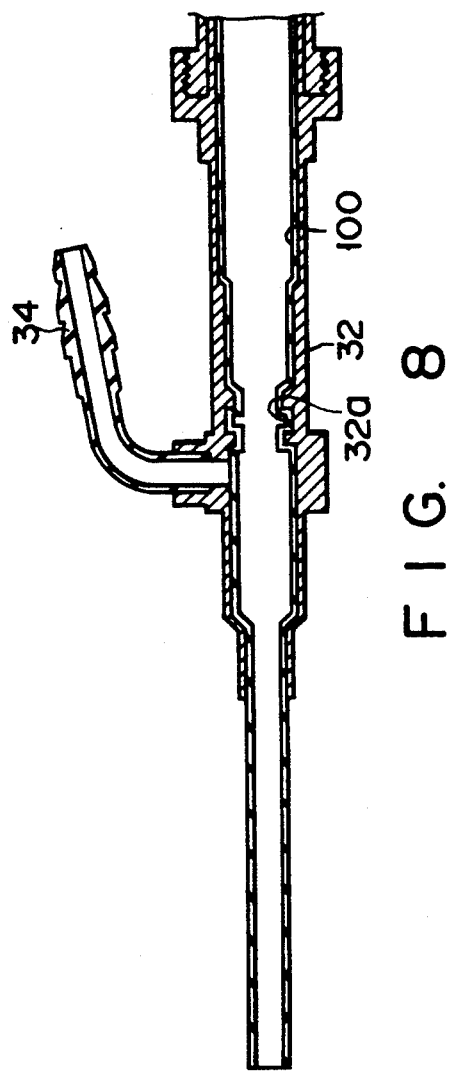
FIG. 7
FIG. 8

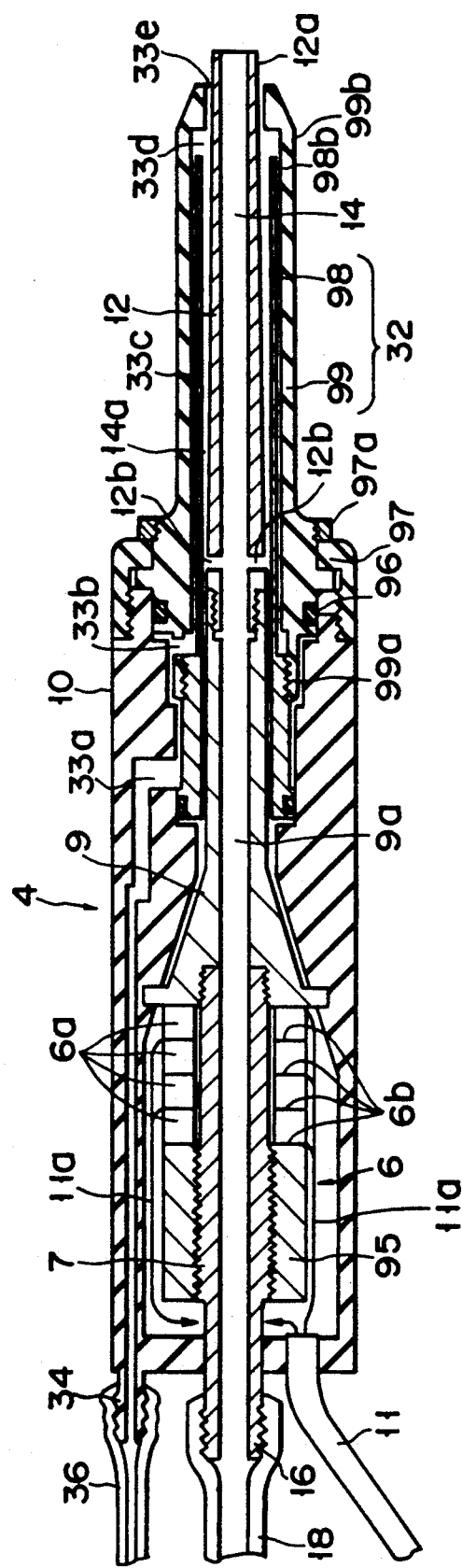
F I G. 12

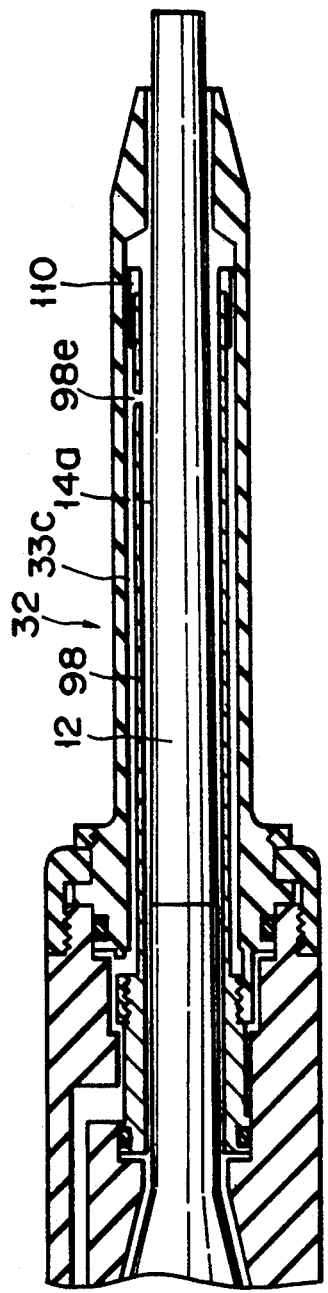
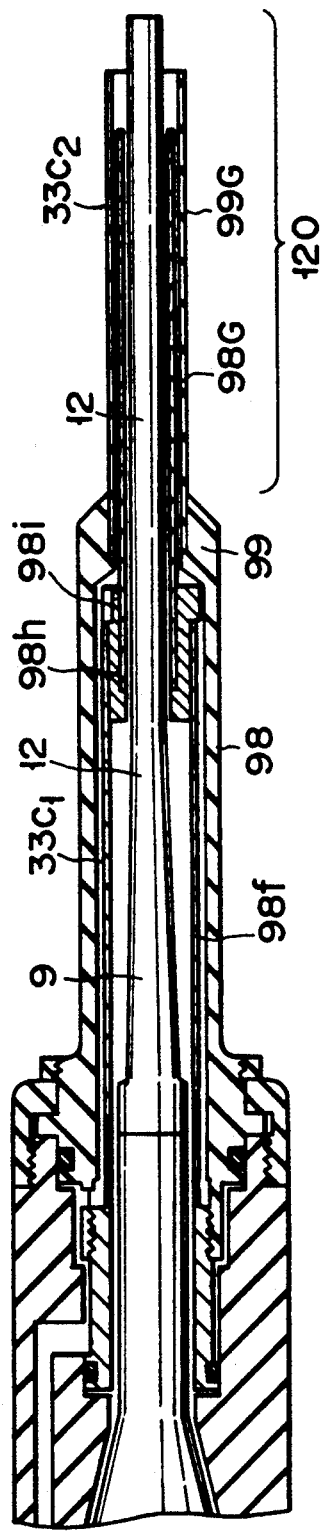
FIG. 15
FIG. 16

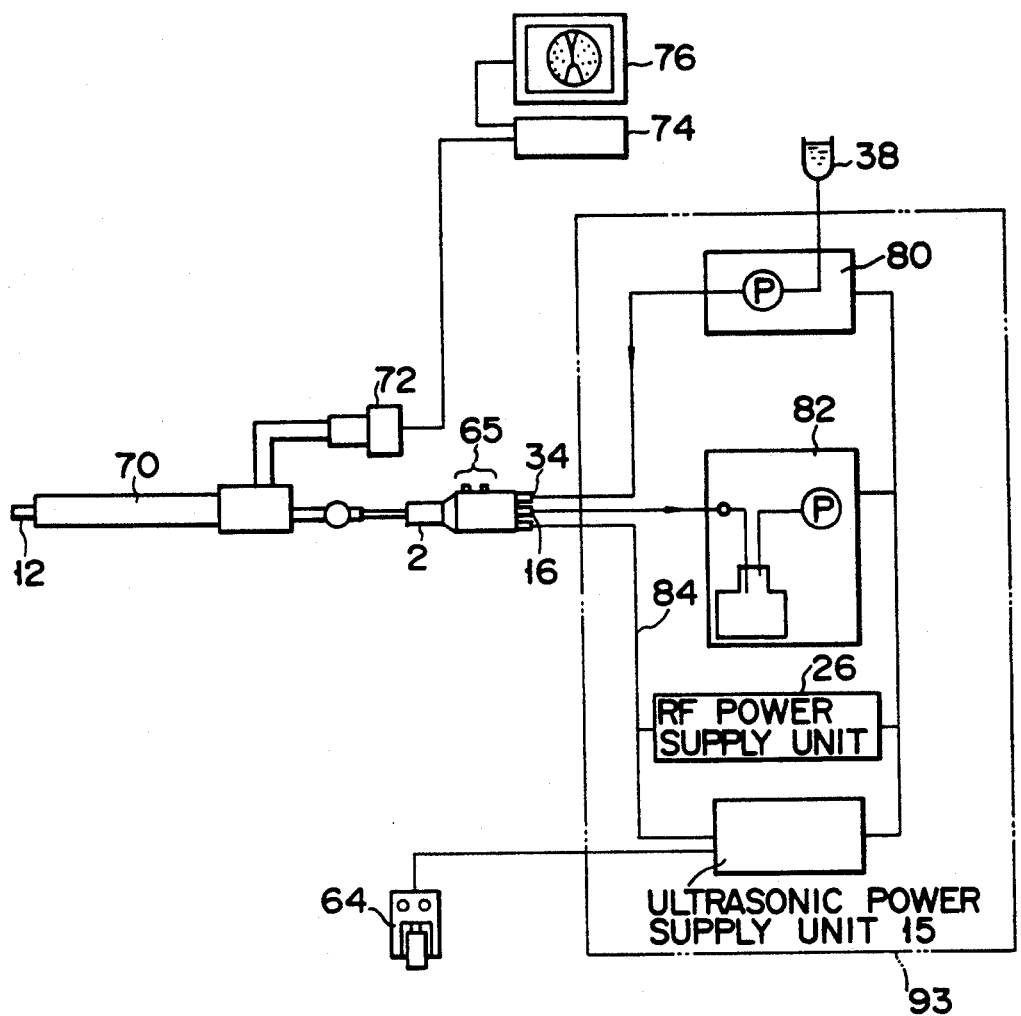
F I G. 18
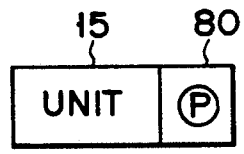 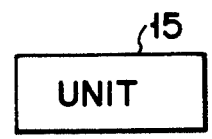
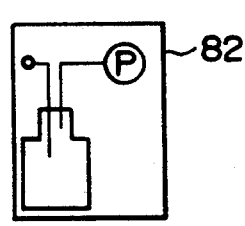 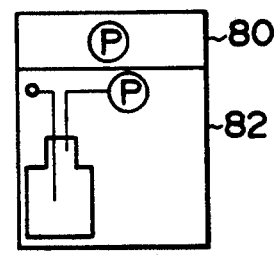
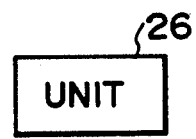 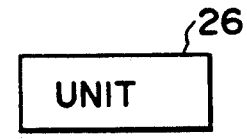
F I G. 19   F I G. 20

ULTRASONIC TREATMENT APPARATUS

BACKGROUND OF THE INVENTION

1. Field of the Invention

The present invention relates to an ultrasonic treatment apparatus for performing a medical treatment of a morbid tissue in a living body by using ultrasonic vibrations and RF currents.

2. Description of the Related Art

In an ultrasonic treatment apparatus, a vibration transmission member is generally coupled to the distal end of an ultrasonic vibrator. The distal end of this vibration transmission member is brought into contact with an internal morbid tissue of a patient to transmit ultrasonic vibrations generated by the ultrasonic vibrator to the tissue through the vibration transmission member, thereby performing a treatment, e.g., the excision of the tissue.

When a tissue of a living body is excised by using the above-described ultrasonic treatment apparatus, the tissue often bleeds.

As a means for eliminating such inconvenience, a technique disclosed in U.S. Pat. No. 4,750,488 is known. In this technique, when a tissue bleeds, an RF current is supplied to a vibration transmission member to stop the bleeding.

Problems, however, are posed in terms of electrical safety, if only an RF current for a hemostatic operation is supplied to a vibration transmission member, as in this conventional technique. More specifically, a current may unintentionally flow in an ultrasonic treatment apparatus itself or peripheral devices for introducing the apparatus into a portion in a living body (patient), such as an endoscope, as well as a patient or an operator, thus causing an electric shock or destruction of the apparatus.

SUMMARY OF THE INVENTION

It is an object of the present invention to provide an ultrasonic treatment apparatus which can prevent a current from flowing in a patient, an operator, or the apparatus itself even if an RF current for a hemostatic operation is supplied to an ultrasonic vibration transmission member, thereby allowing a safe medical treatment.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 1 and 2 show an ultrasonic treatment apparatus according to an embodiment of the present invention, in which FIG. 1 is a sectional view of a handpiece, and FIG. 2 is a schematic view of the overall system;

FIGS. 3 to 17 are sectional views of handpieces according to the second to sixteenth embodiments of the present invention;

FIG. 18 is a schematic view of the overall system; and

FIGS. 19 to 23 are views of various modifications, each showing a case wherein a system is formed into a unit.

DETAILED DESCRIPTION OF THE PREFERRED EMBODIMENTS

Embodiments of the present invention will be described below with reference to the accompanying drawings.

Figure 1:
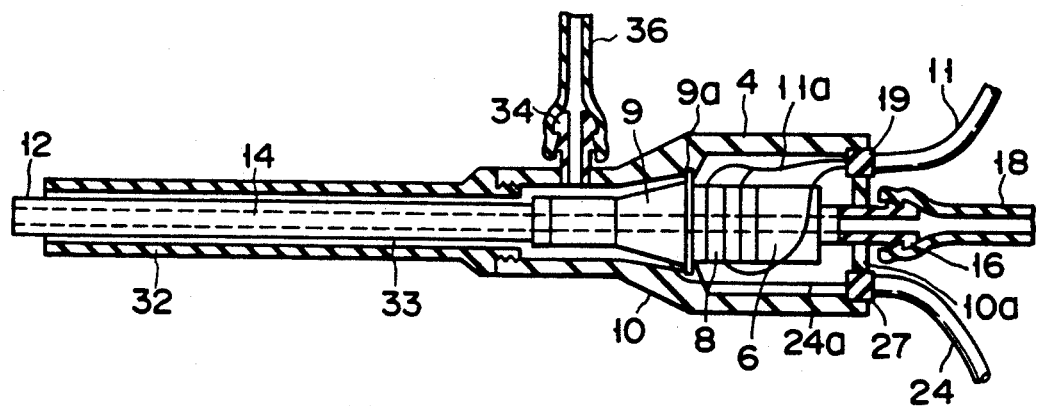
Figure 2:
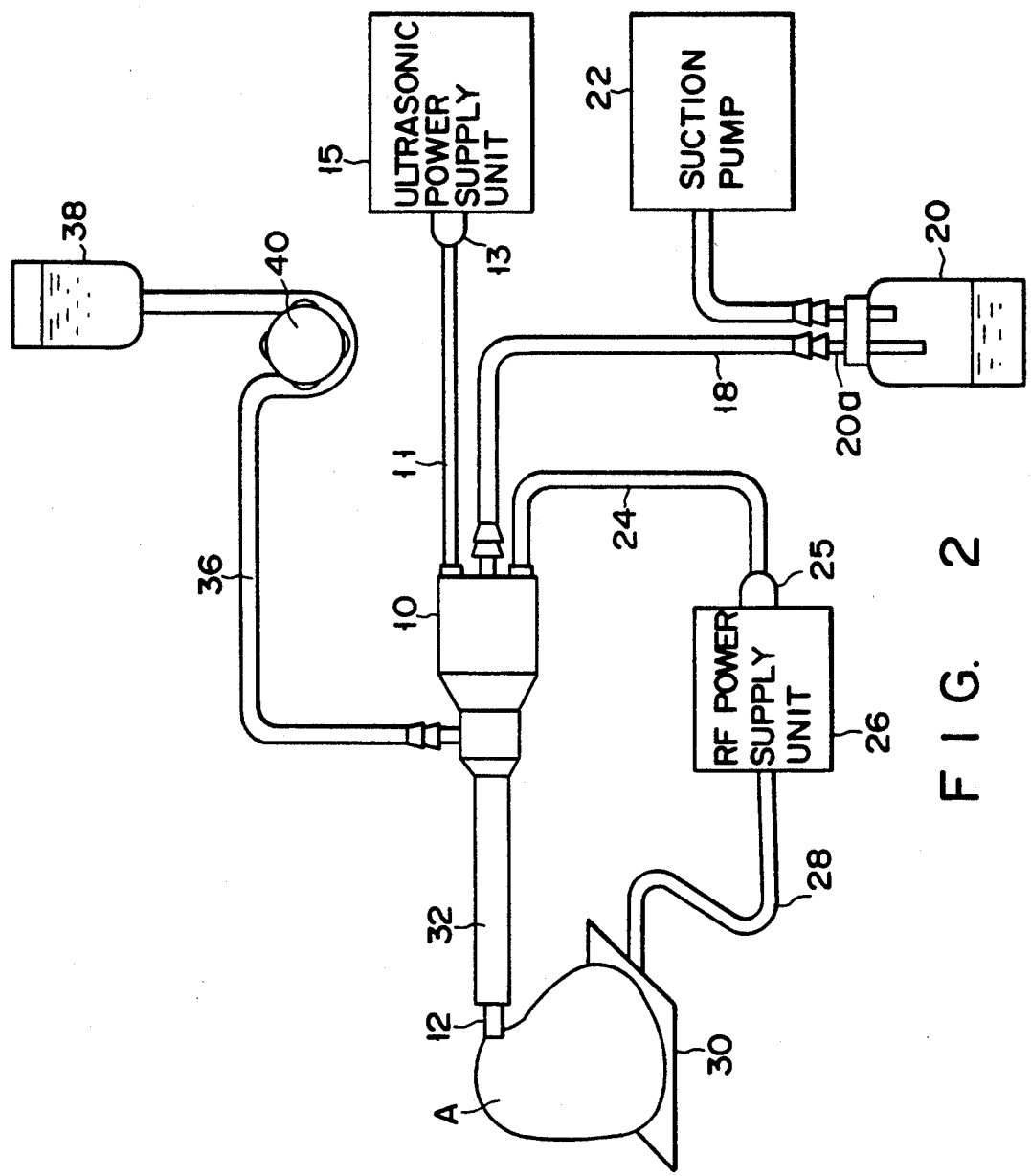

FIGS. 1 and 2 show the first embodiment of the present invention.

As shown in FIG. 1, an ultrasonic treatment apparatus according to the present invention includes a hand piece 2 used for a medical treatment of a morbid tissue in a living body. An ultrasonic vibrator 6 of a Langevin type is arranged in a grip portion 4 of the hand piece 2. This ultrasonic vibrator 6 comprises a horn 9 for amplifying the amplitude of ultrasonic vibrations, and a vibration generating portion 8 formed by alternately stacking piezoelectric elements and electrodes. The vibration generating portion 8 is fastened to the rear end face of the horn 9 by a bolt and a nut (not shown). A flange 9a extends from the outer periphery of a rear end portion of the horn 9. This flange 9a is fixed to a vibrator cover 10 which covers the ultrasonic vibrator 6. Leads 11a of an ultrasonic power supply cord 11 are respectively connected to the electrodes of the vibration generating portion 8. The ultrasonic power supply cord 11 is connected to an ultrasonic power supply unit 15 through a power supply connector 13, as shown in FIG. 2. The distal end of the power supply cord 11 is fixed to a rear wall 10a of the vibrator cover 10 through a power supply cord mouthpiece 19. A vibration transmission member 12 constituted by a hollow metal pipe is fixed to the distal end of the horn 9. Through holes are formed in the horn 9 and the vibration generating portion 8. These through holes and the hollow of the vibration transmission member 12, which communicates with the through holes, constitute a suction path 14. This suction path 14 communicates with a suction mouthpiece 16 fitted in the rear wall 10a of the vibrator cover 10. A suction bottle 20 is connected to this suction mouthpiece 16 through a suction tube 18 and a suction bottle mouthpiece 20a, as shown in FIG. 2. In addition, a suction pump 22 is connected to the suction bottle 20.

A lead 24a of an RF power supply cord 24 is connected to the horn 9. An RF power supply unit 26 is connected to the horn 9 through this RF power supply cord 24 and a connector 25. With this arrangement, an RF current can be supplied to the vibration transmission member 12 fixed to the horn 9. Furthermore, a P plate 30, as an electrode on the living body side, is connected to the RF power supply unit 26 through a P cord 28. This P plate 30 is used in contact with a living body tissue A. The distal end of the RF power supply cord 24 is fixed to the rear wall 10a of the vibrator cover 10 through a mouthpiece 27.

A sheath 32 for covering the vibration transmission member 12 is coaxially fitted in a front portion of the vibration cover 10 with a predetermined space between the sheath 32 and the transmission member 12. A water supply mouthpiece 34 is arranged at a rear end portion of the sheath 32 so as to communicate with a water supply path 33 between the sheath 32 and the vibration transmission member 12. A water supply tank 38 is connected to this water supply mouthpiece 34 through a water supply tube 36, as shown in FIG. 2. A water supply pump 40 constituted by a roller pump is installed midway along this water supply tube 36. A perfusion liquid such as a physiologic saline is supplied to the water supply path 33 by using this water supply pump 40 so as to be discharged from the distal end of the sheath 32. Note that the water supply mouthpiece 34 may be arranged on the sheath 32 side.

In this first embodiment, except for a portion of the vibration transmission member 12 protruding from the distal end of the sheath 32, all the hand piece outer cover members constituted by the sheath 32, the vibrator cover 10, the water supply mouthpiece 34, the suction mouthpiece 16, the ultrasonic power supply cord mouthpiece 19, the RF power supply cord mouthpiece 27, and the like are composed of an electrically insulating material, e.g., a plastic material such as a polyimide resin or a polyether resin.

In the ultrasonic treatment apparatus having the above-described arrangement, ultrasonic vibrations excited by the vibration generating portion 8 are amplified by the horn 9 and are transmitted through the vibration transmission member 12. When the distal end of the vibration transmission member 12 is ultrasonically vibrated and is brought into contact with a morbid tissue A, the morbid tissue A is excised. At the same time, a perfusion liquid is supplied from the water supply tank 38 through the water supply path 33 between the sheath 32 and the vibration transmission member 12. In the process of this operation, a suction operation can be performed by the suction pump 22 through the suction path 14. If a tissue of a living body bleeds during excision of the tissue, an RF current is supplied to the vibration transmission member 12 through the horn 9. When the RF current flows in the bleeding tissue, the bleeding can be stopped by coagulation.

In a treatment using an RF current, if an RF current for a hemostatic operation leaks, the current may flow in the ultrasonic treatment apparatus itself. Hence, a patient and an operator may receive an electric shock or be burned. For this reason, in this embodiment, all the hand piece outer cover members are composed of an electrically insulating material. Therefore, even if an RF current for a hemostatic operation is supplied to the vibration transmission member 12, no current leaks to a patient and an operator, thus allowing a safe medical treatment.

Note that if the suction and water supply tubes 18 and 36, the suction bottle 20 including the mouthpiece 20a, the coatings of the RF and ultrasonic power supply cord, connectors, and all the outer cover members for the water supply system, the suction system, and the power supply system are constituted by insulating members, in addition to the outer cover members of the hand piece 2, the electrical safety can be further improved.

Figure 3:
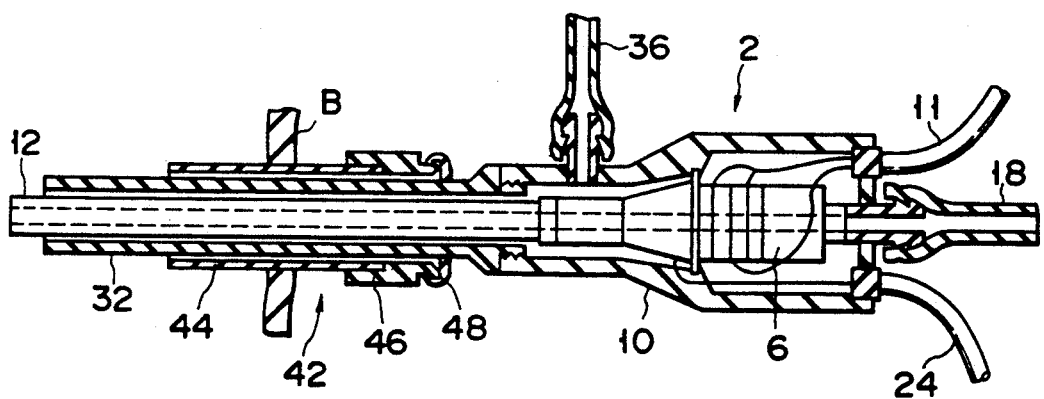

FIG. 3 shows the second embodiment of the present invention. In the second embodiment, in order to use an ultrasonic treatment apparatus endoscopically, a thoracal 42 is attached to the inserting portion of the apparatus. As shown in FIG. 3, the thoracal 42 is mounted on the proximal end portion of a sheath 32. The thoracal 42 comprises a thoracal inserting portion 44, a cylindrical body portion 46 for supporting the inserting portion 44 at its distal end, and a rubber cap 48 for sealing the proximal end opening of the body portion 46.

In the second embodiment, the distal end of a hand piece 2 is inserted in a body cavity through the thoracal 42. In this case, since a body cavity wall B is brought into contact with the thoracal inserting portion 44, at least the outer surface of the thoracal inserting portion 44 consists of an electrically insulating material in order to prevent damage to the body cavity wall B due to heat generated when an RF current is supplied. In consideration of electrical safety for an operator, the outer surface of the thoracal body portion 46 may also be composed of an insulating material so as to further improve the safety. It is apparent that the inner surfaces of the inserting portion 44 and the body portion 46 may be coated with an insulating material, or all the members may be constituted by insulating members, as shown in FIG. 3.

Figure 4:
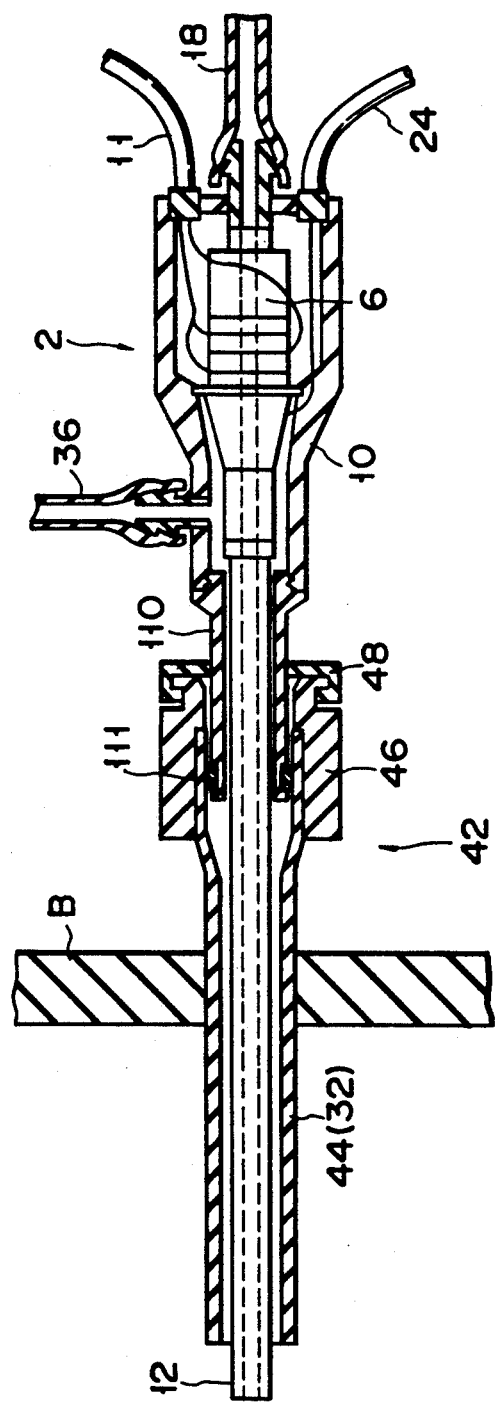

In the third embodiment shown in FIG. 4, a cylindrical member in which a vibration transmission member 12 is housed is not constituted by a sheath but by a thoracal inserting portion 44 and a thoracal attachment 110. The thoracal attachment 110 is constituted by a cylindrical insulating member. The proximal end of the thoracal attachment 110 is coaxially attached to the distal end of a case 10. The thoracal inserting portion 44 consists of an insulating member and has a small-diameter inserting portion which is inserted in a body cavity. The distal end of the inserting portion 44 extends near the distal end of the vibration transmission member 12. The distal end portion of the attachment 110 is slidably inserted in a large-diameter proximal en portion of the thoracal inserting portion 44. A seal means is arranged between the attachment 110 and the proximal end of the thoracal inserting portion 44 to provide a liquid-tight or air-tight seal there-between. This seal means is constituted by an annular groove formed in the outer periphery of the attachment 110, and an O-ring 111 held in the annular groove and positioned between the two members 44 and 110. In this embodiment, since both the thoracal attachment 110 and the thoracal inserting portion 44 are constructed by electrically insulating members, an electric shock to a patient or an operator can be prevented. Unlike the second embodiment, in this embodiment, no sheath is used, and the thoracal inserting portion 44 serves as a sheath to be inserted in a body cavity. Therefore, the diameter of the inserting portion of the third embodiment can be set to be smaller than that of the second embodiment. This reduces an ingression into a patient.

In the third embodiment, since the thoracal body portion 46 is provided with the elastic cap 48 so that the thoracal portion 44 and attachment 110 may be relatively slidable with each other, keeping a light-tight and air tight therebetween, the O-ring 111 for sealing may be omitted.

Figure 5:
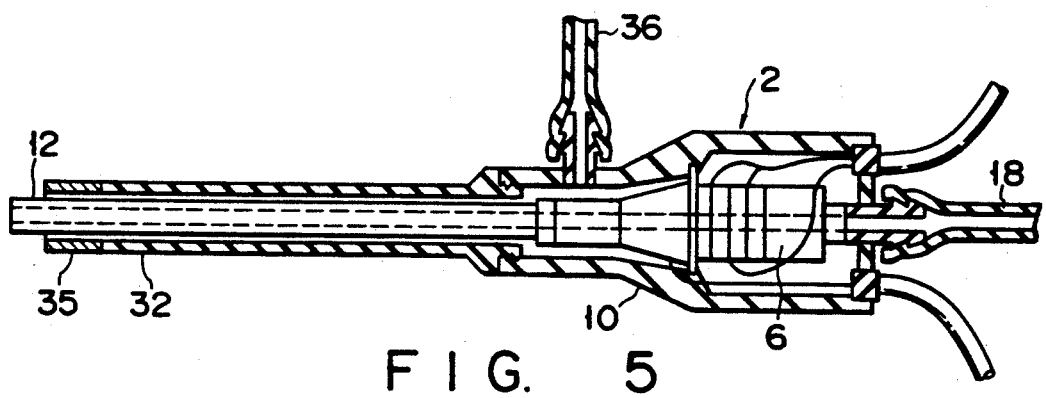

FIG. 5 shows the fourth embodiment of the present invention.

In the fourth embodiment, the distal end portion of a sheath 32 is constituted by a heat resistant insulating member 35 such as an annular ceramic member, thus preventing the sheath end portion from being burned or melted due to heat generated when an RF current flows in a vibration transmission member 12.

Even in a case wherein no RF current is supplied to the vibration transmission member 12, this arrangement can prevent the sheath end portion from being damaged by heat generated upon vibrations of the member 12.

Figure 6:
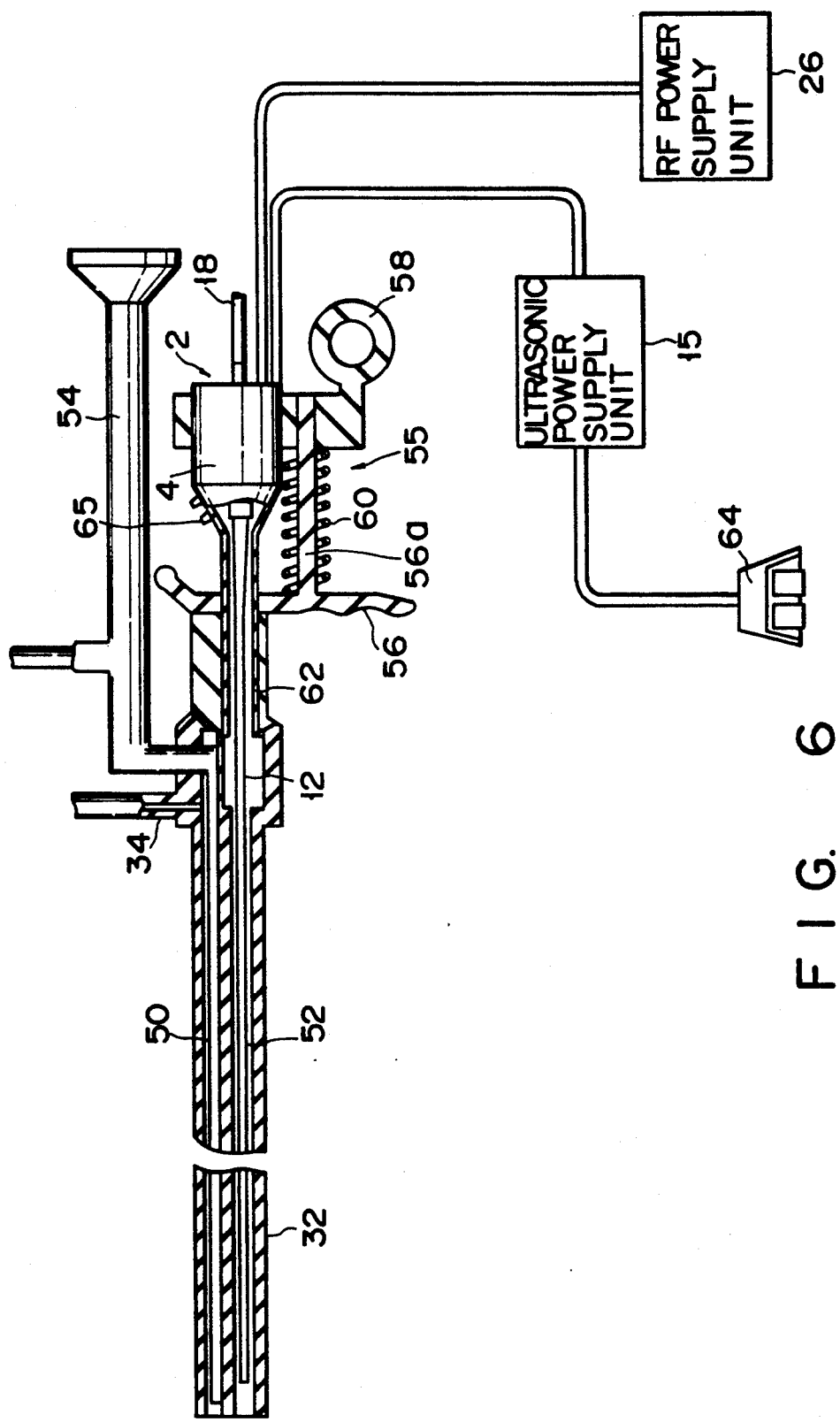

FIG. 6 shows the fifth embodiment of the present invention. In the fifth embodiment, the present invention is applied to an endoscope (hard scope) for introducing an ultrasonic treatment apparatus in a living body. An insertion path 50 and a channel 52 are formed in a sheath 32 to extend parallel to each other. The distal ends of both the insertion path 50 and the channel 52 are open to the front end face of the sheath 32, whereas the proximal end of the former ends midway along the sheath 32, and the proximal end of the latter is open to the rear end face of the sheath 32. An optical viewing tube 54 as an endoscope is inserted into the insertion path 50 from its proximal end side and is fixed therein. The sheath 3 is designed to be separated into a distal end portion and a proximal end portion at the inserting position of the optical viewing tube 54 as a boundary so as to allow the optical viewing tube 54 to be inserted into the insertion path 50, although it is not shown. An inserting portion of the ultrasonic treatment apparatus is inserted into the channel 52 from its proximal end to be reciproced (by a moving mechanism to be described later). A fixed side finger hook portion 56 constituting a working element 55 radially extends from the proximal end portion of the sheath 32. An axial portion 56a extends backward from this finger hook portion 56. A movable side finger hook portion 58 to which a grip portion 4 of the ultrasonic treatment apparatus is fixed is reciprocally fitted on the axial portion 56a. A coil spring 60 is wound around the axial portion 56a of the fixed side finger hook portion 56 so as to bias the movable side finger hook portion 58 in a direction to separate from the fixed side finger hook portion 56, i.e., backward. When the movable side finger hook portion 58 is inserted forward against the biasing force of the coil spring 60, the distal end of a vibration transmission member 12 of the ultrasonic treatment apparatus protrudes from the distal end of the sheath 32.

In the fifth embodiment, the optical viewing tube 54 is inserted/fixed in the insertion portion 50 of the sheath 32, of the endoscope, consisting of an insulating material, and the vibration transmission member 12 is reciprocally inserted in the channel 52. In addition, the vibration transmission member 12 is covered by an attachment 62 coupled to a vibrator cover 10 consisting of an insulating material and to the sheath 32 so as not to be exposed from the proximal end of the sheath 32 upon reciprocal movement in the channel 52. Instead of the insulating sheath 32, the channel 52, of the conductive sheath 32, in which the vibration transmission member 12 is inserted, my be formed by an electrically insulating material.

An ultrasonic power supply unit 15 and an RF power supply unit 26 are connected to a hand piece 2 constituted by the above-described members. In this arrangement, since an ultrasonic vibrator and an RF current are respectively ON/OFF-controlled by a foot switch 64 and a hand switch 65, the operability of the apparatus is improved.

Note that ultrasonic waves may be controlled by a hand switch, and RF currents by a foot switch. In addition, both the switches may be constituted by either hand switches or foot switches. Other basic arrangements, operations, and effects are the same as those in the first embodiment.

FIG. 7 shows the sixth embodiment of the present invention.

A vibrator 6 is formed by alternately stacking annular piezoelectric elements 6a and electrodes 6b and is fastened to the proximal end of a horn 9 having a through hole 9d by a hollow bolt 7. A flange 9a extends from the outer periphery of the proximal end portion of the horn 9. This flange 9a is fixed and held between an inner step portion of a cover 10 and a clamping ring 9b through a spacer 9c and an O-ring by threadably engaging male threads of the ring 9b with female threads formed in the inner surface of the cover 10. The female threads are formed in the inner surface of a front portion of the horn 9, and the male threads are formed in the outer surface of a rear portion of a vibration transmission member 12. These thread portions are threadably engaged with each other to coaxially fix the vibration transmission member 12 to the horn 9.

Figure 9:
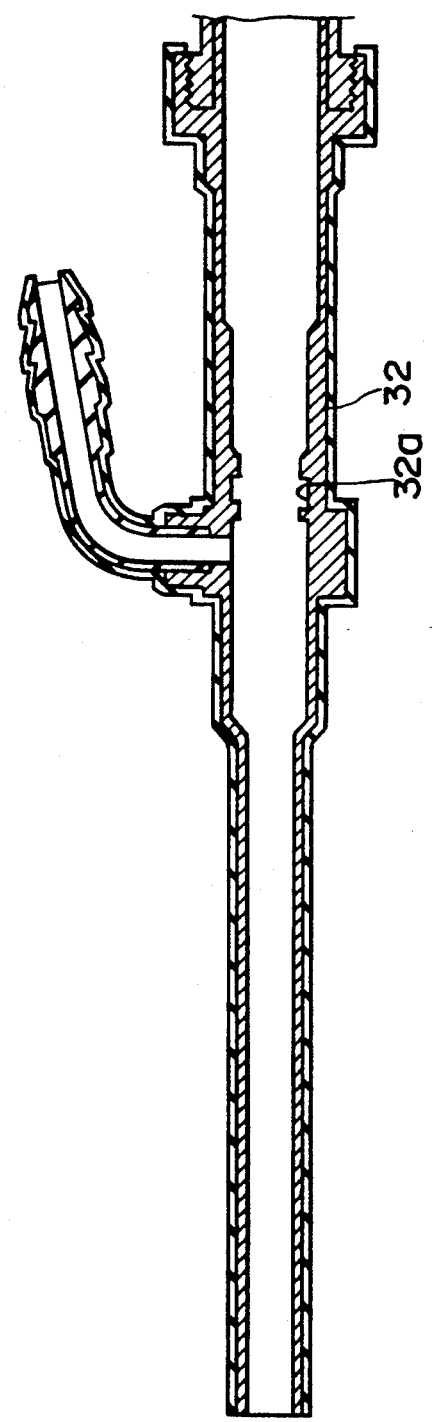

In this embodiment, a sheath 32 is constructed by a member having an insufficient electric insulating property, e.g., a metal. In order to electrically insulate the sheath 32 and the vibration transmission member 12 from each other, the entire outer surface of the vibration transmission member 12 is coated with an insulating film, an insulating tube, or an insulating layer 100. In contrast to this, the inner surface of a sheath 32 in the seventh embodiment shown in FIG. 8 and the outer surface of a sheath in the eight embodiment shown in FIG. 9 are respectively coated with insulating members 100. In the eighth embodiment, although the sheath 32 and a vibration transmission member 12 are not electrically insulated from each other, since the sheath 32 is electrically insulated from the outside, the same effect as in other embodiments can be obtained. This insulating member 100 is composed of an insulating member such as Teflon or polyimide. In the embodiment shown in FIG. 7, a seal means is provided to a rear portion of a water supply path 33 to reliably prevent a liquid from flowing from the water supply path 33 into a cover 10. This seal means comprises an annular groove 32a formed in a portion of the inner surface of the sheath 32 which is located behind a mouthpiece 34, and an O-ring 32b held in the annular groove 32a and located between the sheath 32 and a vibration transmission member 12.

Figure 10:
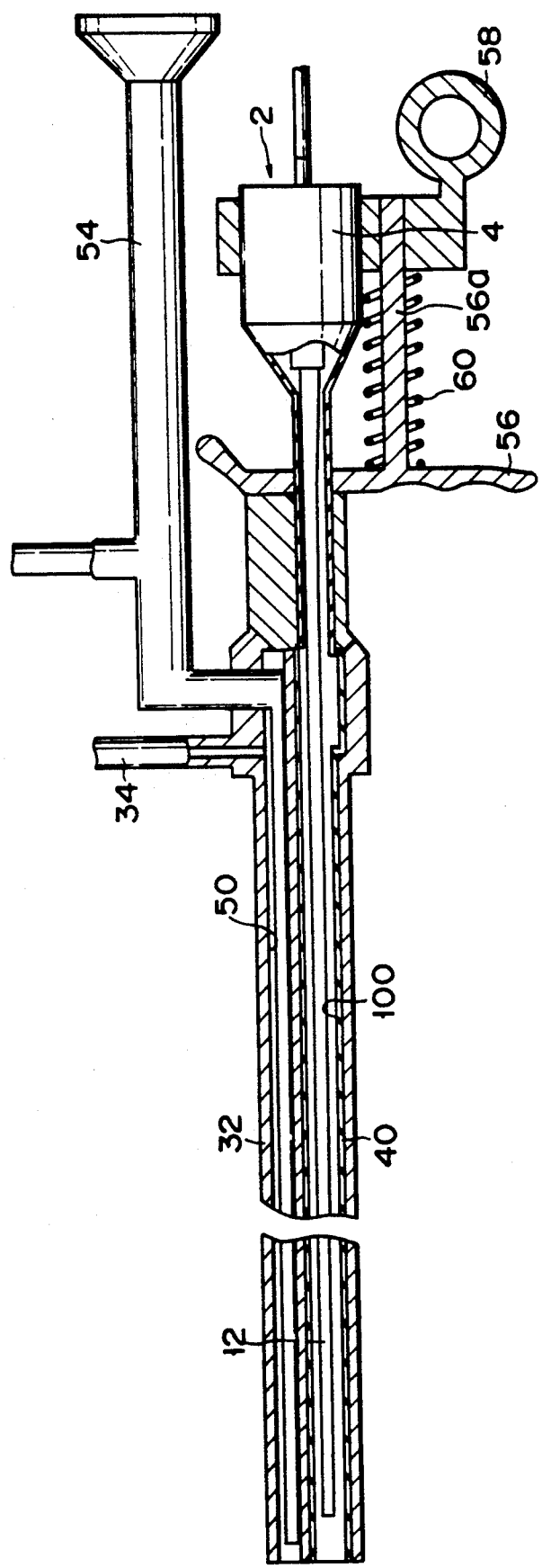

The ninth embodiment shown in FIG. 10 is the same as the embodiment shown in FIG. 6 except for the arrangement of a sheath. That is, the ninth embodiment is an apparatus formed in combination with an endoscope (hard scope). In this embodiment, a sheath 32 consists of a conductive material, e.g., a metal. In order to electrically insulate this sheath 32 from a vibration transmission member 12, similar to the seventh embodiment, the inner surface of the sheath 32 is coated with an insulating film 100. Alternatively, the outer surface of the sheath 32 may be coated with this insulating film.

Figure 11:
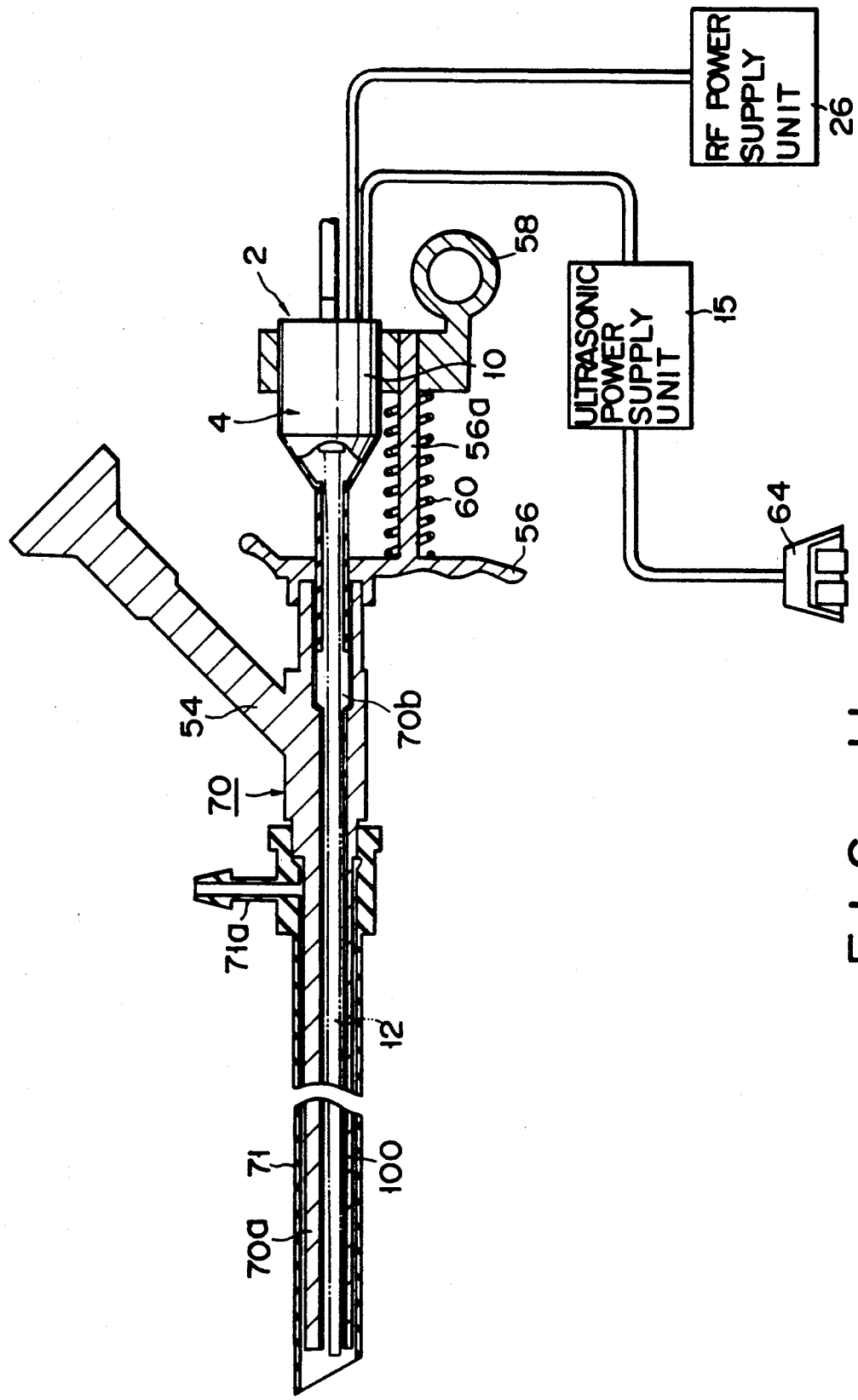

In the tenth embodiment shown in FIG. 11, an inserting portion 70a of an optical viewing tube 54 of an endoscope (hard scope) 70 is used as a sheath. The proximal end portion of this endoscope is integrally formed with the inserting portion 70a using a metal or the like. These portions have coaxial through holes. A channel 70b in which a vibration transmission member 12 is introduced is defined by these through holes. The distal end portion of the vibration transmission member 12 can protrude from the distal end of the channel 70b. The proximal end of the vibration transmission member 12 is open to the rear end of the proximal end portion of the channel 70b. A small-diameter distal end portion of a cover 10 slidably extends into the channel 70b through the opening of this proximal end portion. The vibration transmission member 12 coaxially protrudes from this small-diameter distal end portion. When the small-diameter distal end portion slides in the channel 70b, the distal end portion of the vibration transmission member 12 is retractable from the channel 70b. This endoscope includes a moving mechanism for sliding the small-diameter distal end portion of the cover 10. This moving mechanism is substantially the same as the mechanism shown in FIG. 6, and hence a description thereof will be omitted. The inner surface of the channel 70b of the inserting portion 70a is coated with an insulating film 100 consisting of an insulating material such as Teflon or polyimide. A sheath member 71 is coaxially formed around the inserting portion 70a so as to form a water supply path therebetween. A mouthpiece 71a extends from the proximal end portion of this sheath member 71. A liquid is supplied to the water supply path through the mouthpiece 71a. At least a portion of the sheath member 71 which is inserted in a body is preferably constituted by an insulating member or coated with an insulating film. Instead of forming the insulating film 100 on the inner surface of the channel 70b, exposed portions such as the optical viewing tube 54 and the sheath member 71 may be composed of an insulating material or coated with an insulating film or the channel 70b itself may be formed by an insulating material.

FIG. 12 shows the eleventh embodiment of the present invention. In an ultrasonic treatment apparatus according to this embodiment, an ultrasonic vibrator 6 is arranged in a grip portion 4 of a hand piece 2 and is fixed to a cover 10 by a bolt 7 and a nut 95. A horn 9 for amplifying the amplitude of ultrasonic vibrations is connected to the front end of the ultrasonic vibrator 6. A suction hole 9a is formed along the center axis of the horn 9. The proximal end of the suction hole 9a extends through the ultrasonic vibrator and is connected to a suction pump arranged outside the hand piece 2 through a mouthpiece 16 and a suction tube 18. A probe constituted by a hollow metal member as a vibration transmission member or a vibration transmission member 12 is detachably connected to the distal end of the horn 9. The hollow portion formed in the vibration transmission member 12 constitutes a first suction path 14 communicating with the suction hole 9a.

A sheath 32 is arranged to cover the vibration transmission member 12. The proximal end portion of the sheath 32 is attached to the distal end portion of a cover 10 of the hand piece 2.

An arrangement of the sheath 32 will be described below.

The sheath 32 has a double tube structure constituted by an inner sheath 98 and an outer sheath 99 which covers the inner sheath 98. The inner sheath 98 is only threadably engaged with a rear end portion 99a of the outer sheath 99 to be fixed thereto. The outer sheath 99 is detachably mounted on a housing 10 of the hand piece 2 by a nut 97. An O-ring 96 is arranged between the outer sheath 99 and the cover 10 to provide a liquid-tight seal between the outer sheath 99 and the cover 10. In addition, the nut 97 is fixed by a fastening nut 97a threadably engaged with the outer sheath 99.

With this arrangement, the inner sheath 98 is concentrically fitted on a vibration transmission member 12 with a gap formed between the inner sheath 98 and the vibration transmission member 12. In addition, the outer sheath 99 is concentrically fitted on the vibration transmission member 12 and the inner sheath 98 with a gap formed between the outer sheath 99 and the inner sheath 98. The gap between the inner and outer sheaths 98 and 99 and the gap between the vibration transmission member 12 and the inner sheath 98 respectively serve as a water supply path 33c and a second suction path 14a. A plurality of water supply communicating holes 33b are formed in the proximal end portion of the outer sheath 99 at predetermined intervals in the circumferential direction so as to extend through an annular side wall of the outer sheath 99. The water supply paths 33a and 33c communicate with each other through these water supply communicating holes 33b. The water supply path 33a is connected to a water supply pump arranged outside the hand piece 2 through a mouthpiece 34 and a water supply tube 36. A plurality of suction communicating holes 12b are formed in the proximal end portion of the vibration transmission member 12 at predetermined intervals in the circumferential direction so as to extend through an annular side wall of the vibration transmission member 12. The first and second suction paths 14 and 14a communicate with each other through these suction communicating holes 12b.

Note that a suction communicating hole may be formed to extend through a side wall of the distal end portion of the horn 9 to cause the suction hole 9a and the second suction path 14a to communicate with each other.

The inner sheath 98 is shorter than the outer sheath 99 so that the distal end of the inner sheath 98 is located inward from that of the outer sheath 99. With this arrangement, the water supply path 33c and the second suction path 14a communicate with each other through an annular communicating path 33d formed between the distal end of the inner sheath 98 and the distal end of the outer sheath 99. A gap 33e communicating with the outside is defined between the inner surface of the distal end portion of the outer sheath 99 and a distal end portion 12a of the vibration transmission member 12.

The horn 9 is connected to an RF power supply (not shown) arranged outside the hand piece 2 through an A cord 11. Therefore, an RF current can be supplied to the vibration transmission member 12 fixed to the horn 9.

In the eleventh embodiment, the inner sheath 98 consists of a metal material, while all the hand piece cover members constituted by, e.g., the cover 10 of the hand piece 2, the outer sheath 99, and the nut 97 consist of an insulating material except for a portion of the vibration transmission member 12 which protrudes from the distal end of the sheath 32. As an insulating material, for example, a plastic material such as a polyimide resin, a polyether resin, or a fiber reinforced epoxy resin, or a ceramic material is used.

An operation of the ultrasonic treatment apparatus according to the eleventh embodiment of the present invention will be described below.

In the ultrasonic treatment apparatus having the above-described arrangement, ultrasonic vibrations generated by the ultrasonic vibrator 6 are amplified by the horn 9 and are transmitted to the vibration transmission member 12. When the distal end portion 12a of the vibration transmission member 12 is brought into contact with a morbid tissue, the tissue is emulsified and excised by the ultrasonic vibrations. The excised tissue pieces are removed by suction from the body through the suction path 14.

A perfusion liquid pumped by the water supply pump is supplied to the distal end portion of the vibration transmission member 12 through the water supply path 33a, the water supply communicating hole 33b, and the water supply path 33c. A portion of the perfusion liquid flows into a body cavity through the gap 33e between the vibration transmission member 12 and the outer sheath 99 to clean the treated portion. The rest of the perfusion liquid flows in the second suction path 14a to directly cool the vibration transmission member 12 which is heated by the ultrasonic vibrations. Thereafter, the liquid flows into the first suction path 14 through the suction communicating hole 12b to be discharged from the mouthpiece 16. If the morbid tissue bleeds during excision, an RF current is supplied to the vibration transmission member 12 through the horn 9. When the current flows in the bleeding portion, the bleeding can be stopped by coagulation. In this embodiment, since the cover 10 of the hand piece 2, the outer sheath 99, and the like consist of an insulating material, no RF current leaks to an operator or a tissue other than a morbid portion upon a power ON operation. In addition, since the inner sheath 98 is composed of a metal material to reduce its diameter, a reduction in ingression into a patient is ensured.

Furthermore, in the structure of the sheath 32, the inner sheath 98 consists of a metal material, while the outer sheath 99 consists of a plastic material. Although the two sheaths 98 and 99 have different thermal expansion coefficients, since they are coupled to each other at a portion of a rear end portion 99a of the outer sheath 99 and are not fixed at a distal end portion 99b of the outer sheath 99, free thermal expansion of these sheaths 98 and 99 is allowed. With this arrangement, even if a sterilizing operation using high-pressure steam is performed while the inner and outer sheathes 98 and 99 are combined, destruction of the sheaths does not occur.

Furthermore, in this embodiment, the inner sheath 98 is detachably fixed to the outer sheath 99. In a normal operation, therefore, the inner and outer sheaths 98 and 99 can be attached/detached together by attaching/detaching the outer sheath 99 to/from the cover 10 of the hand piece 2 using the nut 97.

In contrast to this, the sheaths 98 and 99 can be easily and reliably cleaned by detaching the inner sheath 98 from the outer sheath 99 even if blood, humor, tissues of a living body, and the like are left in the water supply path 33c.

Figure 13:
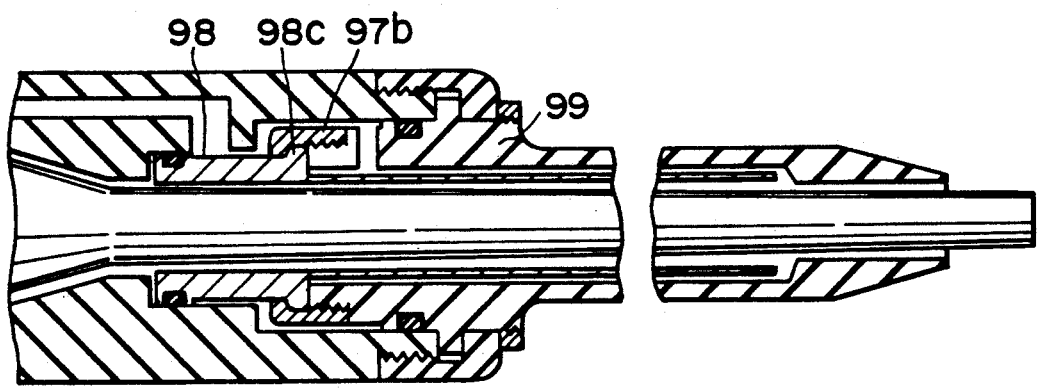

FIG. 13 shows the twelfth embodiment of the present invention. In a connecting structure for inner and outer sheaths 98 and 99 of this embodiment, a flange 98c is formed on the outer periphery of the inner sheath 98 so as to be fastened to the outer sheath 99 by a nut 97b. Other arrangements of the twelfth embodiment are the same as those of the eleventh embodiment.

Figure 14:
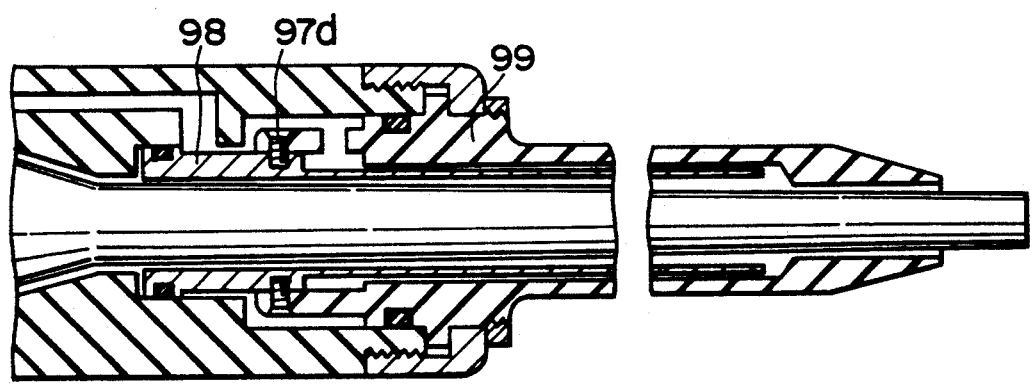

FIG. 14 shows the thirteenth embodiment of the present invention. In a connecting structure for inner and outer sheaths 98 and 99 of this embodiment, the inner sheath 98 is fixed to the outer sheath 99 by a plurality of screws 97d. Note that rivets or pins may be used in place of the screws 97d.

FIG. 15 shows the fourteenth embodiment of the present invention. In this embodiment, an annular spacer 110 having an outer diameter slightly smaller than the inner diameter of the outer sheath 99 is attached to the distal end portion of an inner sheath 98. In addition, a plurality of through holes 98e are formed in the peripheral wall of a portion of the inner sheath 98 which is located closer to the proximal end than the spacer 110 so as to cause a water supply path 33c and a suction path 14a to communicate with each other.

This spacer 110 serves to prevent an axial deviation between the inner and outer sheaths 98 and 99, thus preventing generation of heat or abrasion due to contact between the inner sheath 98 and an ultrasonically vibrated vibration transmission member 12.

In addition, since the spacer 110 is formed to have an outer diameter slightly smaller than the inner diameter of the outer sheath 99, so that the relative movement of the inner and outer sheaths 98 and 99 in the axial direction is not restricted, attachment/detachment of the inner and outer sheaths 98 and 99 can be easily performed. Even if a sterilizing operation using high-pressure steam is performed while the inner and outer sheaths 98 and 99 are combined, no thermal stress acts on these sheaths, thus preventing their destruction.

FIG. 16 shows the fifteenth embodiment of the present invention. In this embodiment, a vibration transmission member 12 and a horn 9 are integrally composed of a metal material such as titanium alloy. A sheath having a double tube structure is formed by joining tubular members having different diameters, as inner and outer sheaths 98 and 99, at a boundary portion between the horn 9 and the vibration transmission member 12, thereby reducing the diameter of an inserting portion 120 to be inserted in a body cavity.

In addition, an annular intermediate member 98h is arranged between joining portions of a large-diameter proximal end portion 98f of the inner sheath 98 and a small-diameter distal end portion 98g thereof so as to prevent an axial deviation between the inner and outer sheaths 98 and 99. The intermediate portion 98h is formed to have an outer diameter slightly smaller than the inner diameter of the outer sheath 99 so that the relative movement of the inner and outer sheaths 98 and 99 in the axial direction is not restricted.

Furthermore, a plurality of water supply grooves 98i are formed in the intermediate member 98h at predetermined intervals to extend in the axial direction, and a proximal end portion $33c_1$ and a distal end portion $33c_2$ of a water supply path communicate with each other through the water supply grooves 98i. The water supply grooves 98i are formed to have a total sectional area larger than the sectional area of the proximal end portion $33c_1$ of the water supply path so as not to interfere with the flow of a perfusion liquid.

A distal end inserting portion 99G of the outer sheath 99 has a small diameter and extends near the distal end of the vibration transmission member 12.

Figure 17:
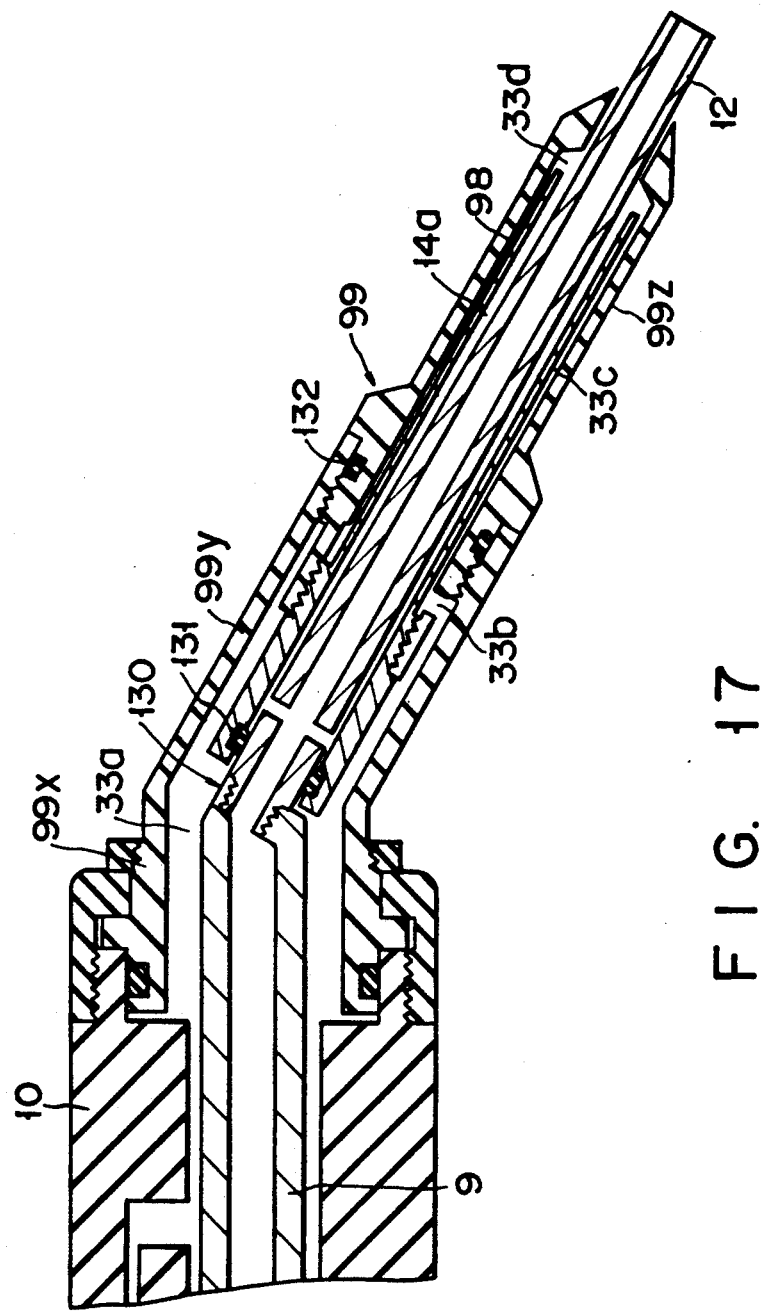

FIG. 17 shows the sixteenth embodiment of the present invention. In this embodiment, a horn 9 and a vibration transmission member 12 are screwed to each other at a predetermined angle. An outer sheath 99 comprises a proximal end portion 99x connected to a cover 10 and coaxially extending with respect to the cover 10, an intermediate portion 99y integrally connected to the distal end of the proximal end portion 99x and extending at an obtuse angle with respect to the proximal end portion 99x, and a small-diameter distal end portion 99z threadably engaged with the intermediate portion 99y. A bent portion between the horn 9 and the vibration transmission member 12 is covered by the distal end of the proximal end portion 99x and the proximal end of the intermediate portion 99y. The proximal end portion of the inner sheath 98 is threadably engaged with the outer sheath 99 and coaxially extends with respect to the distal end portion 99z. O-rings 131 and 132 are respectively inserted between the proximal end portion of the inner sheath 98 and the vibration transmission member 12 and between the intermediate portion 99y and the distal end portion 99z so as to provide a liquid-tight seal therebetween.

In this embodiment, therefore, a perfusion liquid flowing from a water supply path 33a in the cover 10 of a hand piece 2 flows into a water supply path between the proximal end portions of both sheathes 98, 99. The liquid then flows into a double sheath water supply path 33c defined by the distal end portions of the sheaths 98, 99 through a hole or holes 33b. The perfusion liquid flows in the water supply path 33c in the same manner as described in the first embodiment.

In the sixteenth embodiment, the water supply path 33a and a second suction path 14a are liquid-tightly separated from each other by the O-ring 131 so that a portion of the sheath located closer to the proximal end than a bent connecting portion 130 between the horn 9 and the vibration transmission member 12 has a single tube structure. Since the bent portion has a simple sheath structure, the outer sheath 99 can be easily attached/detached to/from the cover 10.

FIG. 18 shows an ultrasonic treatment system incorporating the ultrasonic treatment apparatus according to the present invention. This treatment system has an endoscope 70. A TV camera 72 is connected to an eyepiece portion of the endoscope 70. A TV control unit 74 and a monitor 76 are connected to the TV camera 72. With this arrangement, an operator can perform a medical treatment by using the ultrasonic treatment apparatus while watching the monitor 76. Alternatively, the operator may perform a medical treatment while directly viewing a portion of interest through the eyepiece portion of the endoscope 70 without connecting the TV camera 72 to the eyepiece portion.

The endoscope 70 has a channel (not shown) in which the inserting portion of the hand piece 2 of the ultrasonic treatment apparatus is inserted. A medical treatment of a portion to be treated can be performed by causing the distal end of the vibration transmission member 12 of the hand piece 2 to protrude from the distal end of the endoscope 70.

A water supply pump unit 80 (including the water supply pump 40) and a suction pump unit 82 (including the suction bottle 20 and the suction pump 22) are respectively connected to the water supply mouthpiece 34 and the suction mouthpiece 16 of the hand piece 2. A signal cable 84 (the cords 11 and 24) is connected to the hand piece 2. The RF power supply unit 26 and the ultrasonic power supply unit 15 are connected to the signal cable 84. As described above with reference to FIG. 6, the hand piece 2 includes the hand switch 65, and the foot switch 64 is connected to the ultrasonic power supply unit 15. Therefore, ON/OFF control of ultrasonic outputs, RF outputs, and water supply and suction operations can be performed by using the hand switch 65 and the foot switch 64.

Although each switch can be arbitrarily assigned to the control of a specific unit, in this embodiment, RF outputs are ON/OFF-controlled by the hand switch 65, while ultrasonic outputs and water supply and suction operations are ON/OFF-controlled by the foot switch 64. RF outputs can be ON/OFF-controlled by selecting at least one of the following modes upon a switching operation: an excision mode, a coagulation mode, and a composite mode of the excision and coagulation modes. In the ultrasonic treatment system having such an arrangement, a medical treatment by means of ultrasonic vibrations can be endoscopically performed, and at the same time an RF medical treatment can be performed.

That is, since multiple functions can be realized by a single probe, cumbersome operations such as replacement of treatment apparatuses need not be performed. This increases the operability of the system and reduces a treatment time. In addition, since the respective components are formed into units, i.e., the water supply unit, the suction pump unit, the RF power supply, and the ultrasonic power supply, necessary units can be selected in accordance with a treatment purpose. This arrangement provides an improvement in economy and reduces limitations in terms of the space of an operating room.

Switching operation of the respective functions can be performed by selectively using the hand switch and foot switch, thus improving the operability of the system.

FIGS. 19 to 23 respectively show modifications of an external unit 93 in the ultrasonic treatment system. In these modifications, the combination of the units described above is variously changed.

FIG. 19 shows the first modification. In this modification, the ultrasonic power supply unit 15 and the water supply pump unit 80 are integrated. When the ultrasonic treatment apparatus is used, the vibration transmission member 12 must be cooled down, and an operation field must be cleaned, thus requiring the ultrasonic power supply unit 15 and the water supply pump unit 80 in most cases. A failure to cool the vibration transmission member 12 may cause damage to the member 12, injury to a morbid portion of a patient due to heat, and the like. Such danger can be prevented by integrating the ultrasonic power supply unit 15 and the water supply pump unit 80.

FIG. 20 shows the second modification. In this modification, the water supply pump 80 and the suction pump unit 82 are integrated. In an endoscopic operation, an operation field is generally cleaned by a perfusion liquid. Furthermore, in a recent operation, a tissue of a living body is excised and separated by the pressure of a perfusion liquid which is caused to flow at a high pressure. In such a case, a water supply pump unit and a suction pump unit are required. A pump unit obtained by integrating the water supply pump unit and the suction pump unit can be used as a pump unit capable of water supply and suction operations in a variety of fields as well as in an ultrasonic medical treatment.

Figure 21:
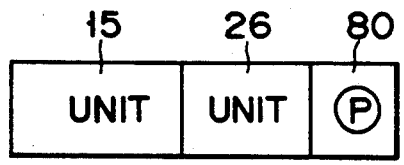
Figure 21:
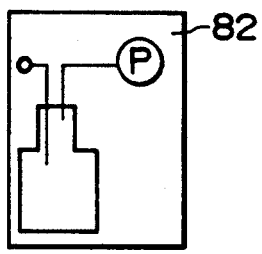

FIG. 21 shows the third modification. In this modification, the water supply pump 80, the RF power supply unit 26, and the ultrasonic power supply unit 15 are integrated. With this integration, a single apparatus allows treatments by means of ultrasonic waves and RF currents, thus widening the application range of operations.

Figure 22:
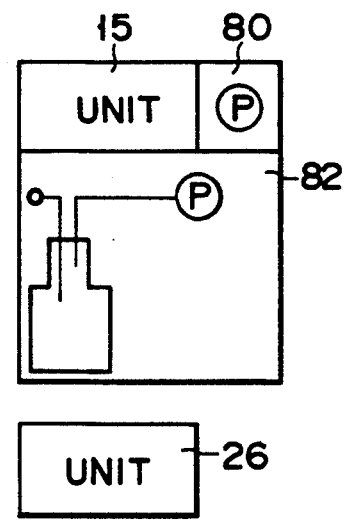

FIG. 22 shows the fourth modification. In this modification, the ultrasonic power supply unit 15, the water supply pump unit 80, and the suction pump unit 82 are integrated. In the fourth modification, an ultrasonic medical treatment and cleaning of an operation field by water supply and suction operations can be performed by a single apparatus.

Figure 23:
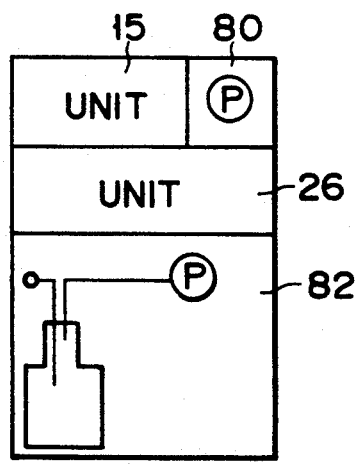

FIG. 23 shows the fifth modification. In this modification, all the units are integrated. By integrating all the units into a compact unit, the occupied space in an operation room can be reduced, and the portability of the unit can be improved. Note the present invention is not limited to the above modifications. For example, the respective units may be formed into modules so that necessary modules can be mounted in a storage rack as needed.

As has been described above, in the ultrasonic treatment apparatus according to the present invention, sufficient insulation is provided to the hand piece to improve its electric safety. In addition, since no metal portions are exposed outside except for the distal end portion of the vibration transmission member, even if a conductive physiologic saline is used as a perfusion liquid, injuries such as a burn can be prevented.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic treatment apparatus comprising:
high-frequency current generating means for generating a high-frequency current; and
a hand piece comprising:
 a hollow cylindrical member having an opening and an outer surface;
 ultrasonic vibration generating means arranged in said hollow cylindrical member, for generating ultrasonic vibrations;
 first transmitting means arranged in said hollow cylindrical member, said first transmitting means having an end portion thereof that is externally exposed from said opening of said hollow cylindrical member, said first transmitting means externally transmitting said ultrasonic vibrations generated by said ultrasonic vibration generation means, through said externally exposed end portion thereof;
 second transmitting means for transmitting said high-frequency current from said high-frequency current generating means to said first transmitting means; and
 at least one mouthpiece provided on said hollow cylindrical member, for supplying water from a water supply means into said hollow cylindrical member through said at least one mouthpiece, said water then being discharged from said hollow cylindrical member through said opening of said hollow cylindrical member;
 all of said outer surfaces of said hollow cylindrical member as well as said at least one mouthpiece being formed of an insulating material, said insulating material preventing said high-frequency current transmitted by said first transmitting means from leaking externally through said hollow cylindrical member and said at least one mouthpiece;
 said first transmitting means having a cylindrical shape, and said first transmitting means including a probe having a suction path defined therein;
 said hollow cylindrical member including;
  an inner sheath extending along said probe and covering said probe to define a first flow path therebetween;
  an outer sheath extending along said inner sheath and covering said inner sheath to define a second flow path therebetween;
  said outer sheath having an end portion where a distal end portion of said probe is externally exposed;
  means for causing said suction path defined in said probe to communicate with said first flow path at proximal end portion of said probe; and
  means for causing said first flow path to communicate with said second flow path;
 said inner sheath comprising an electrically conductive member, and said outer sheath comprising an insulating member; and
 said apparatus further comprising connecting means for detachably connecting said inner and outer sheaths at respective proximal end portions thereof, thereby enabling a distal end portion of each of said inner and outer sheaths to be free;
 whereby said insulating material prevents high-frequency current from leaking along a flow path of said water as said water is discharged through said opening of said hollow cylindrical member.

2. An apparatus according to claim 1, wherein said hollow cylindrical member is formed of the insulating material.

3. An apparatus according to claim 2, further comprising at least one external connecting portion extending from said hollow cylindrical member, said at least one external connecting portion also being formed of the insulating material.

4. An apparatus according to claim 1, further comprising an insulating member covering an outer surface of said first transmitting means.

5. An apparatus according to claim 1, further comprising an insulating member covering at least one of an inner and the outer surfaces of said hollow cylindrical member.

6. An apparatus according to claim 1, wherein:
said ultrasonic vibration generating means includes a vibrator;
said first transmitting means includes a cylindrical probe and a horn connecting said probe to said vibrator; and
said hollow cylindrical member includes a cylindrical portion that covers said probe except for an end portion of said probe, said cylindrical portion being insertable into a body cavity; and
a case covering said vibrator, said case being arranged outside the body cavity.

7. An apparatus according to claim 6, wherein said cylindrical portion of said hollow cylindrical member comprises:
a cylindrical main body arranged on an end portion of said cylindrical portion; and
a portion of said case, positioned on a side of said cylindrical portion that is slidably insertable into said cylindrical main body.

8. An apparatus according to claim 6, further comprising means for detachably connecting an end portion of said case to said hollow cylindrical member.

* * * * *